June 20, 1939. J. H. NICOLAS Plant Pat. 331
ROSE PLANT
Filed Dec. 10, 1938
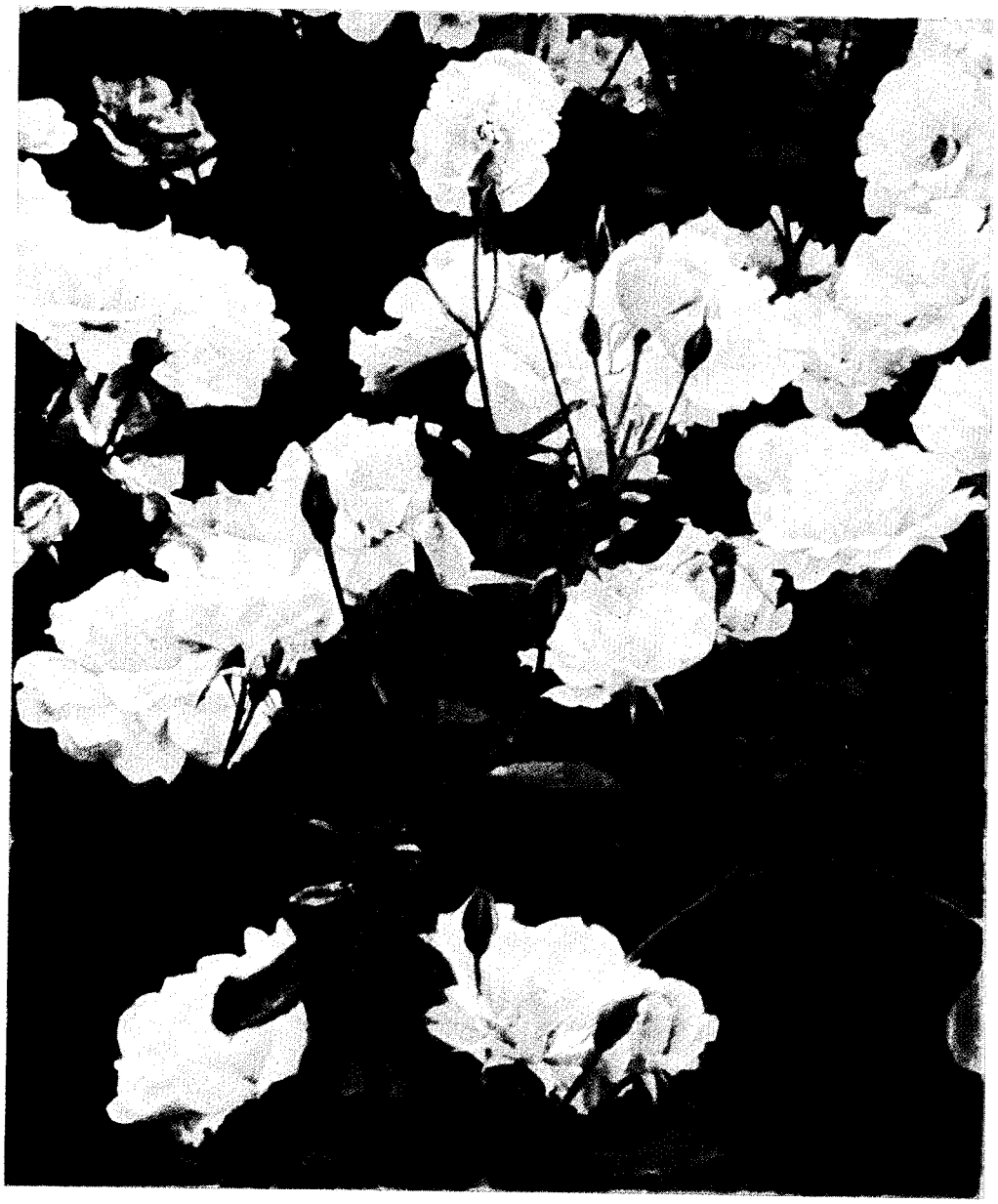
Inventor
Jean H. Nicolas
By Fannie Nicolas
administratrix of the estate
of Jean H. Nicolas, deceased
By Robb & Robb
attorneys Patented June 20, 1939

UNITED STATES PATENT OFFICE

331

ROSE PLANT

Jean H. Nicolas, deceased, late of Newark, N. Y., by Fannie Nicolas, administratrix, Newark, N. Y., assignor to Jackson & Perkins Company, Newark, N. Y.

Application December 10, 1938, Serial No. 245,033

1 Claim. (Cl. 47—61)

The present invention relates to a new and distinct variety of rose plant of the Polyantha class, resulting from a cross of Rev. F. Page Roberts x Echo.

It is believed that this new variety is different from any other rose now in cultivation in many respects.

Primarily in habit of growth, the plant is firmly compact but bushy and this characteristic together with the novel pink color of the large flowered clustered blooms distinguish it from all others in the over blooming Polyantha group.

A further notable feature resides in the plant's habit of blooming continuously and producing many 2½" to 3" flowers in large clusters.

The plant has been asexually reproduced and its novel characteristics above referred to have been found to be firmly established.

The following is a detail description of the new variety, all references to color being in accord with Ridgway's Color Standard:—

Parentage:

*Seed parent.*—Rev. F. Page Roberts.

*Pollen parent.*—Echo.

Classification:

*Botanic.*—Polyantha.

*Commercial.*—Floribunda.

*Flower*

(Observations made at Newark, New York, in the morning of June 23, 1938.)

Blooming habit:

Recurrent—continuous.

*Other habit.*—A continuous shower of blooms.

Bud:

*Size.*—Medium.

*Form.*—Ovoid. Is not affected by wet or hot weather.

*Color.*—When sepals first divide—Plate 13, Acajou Red. When petals begin to unfurl—Plate 13, Jasper Pink. When half blown: Inside of petals—Plate 13, Venetian Pink. Reverse of petals—Plate 13, Alizarine Pink.

*Sepals.*—Serrated, "hood" above bud. Curl back when bud half open.

*Calyx.* — Shape — funnel. Size — broad. Aspect—glandular.

*Peduncle.*—Length—medium. Aspect—prickly. Color—Plate 5, Cosse Green. Strength—erect.

*Opening.*—Bud opens well. Is not affected by adverse conditions.

Bloom:

*Size.*—Medium.

*Average size when fully expanded.*—Two and one-half to three inches.

*Borne.*—In flat clusters.

*Stems.*—Medium length, strong.

*Form.*—When first open — cupped. Permanence—retains its form to the end.

*Petalage.*—Double (full but open center). Number of petals under normal conditions—35 to 40.

*Color.*—Center of flower—Plate 13, Flesh Pink. Outer petals—Plate 13, Venetian Pink. Base of petals (aiglet)—Plate 5, Sulphur Yellow. Inside of petals—Plate 14, Pale Flesh color. Reverse of petals—Plate 13, Venetian Pink.

*Variegations.*—None.

*Discoloration.*—General tonality— Fades gracefully from Plate 13, Venetian Pink to Plate 14, Pale Flesh color.

Petals:

*Texture.*—Thick. Is not affected by wet or hot weather.

*Appearance.*—Inside—shiny. Outside—shiny.

*Form.*—Oval, notched.

*Arrangement.*—Informal (with "rags" in center). Petaloids in center—many.

*Persistence*—Drop off cleanly.

*Fragrance.*—Moderate. Nature—Tea (average Hybrid Tea scent).

*Lasting quality.*—On the plant—very long. As cut flower—long.

Genital organs:

*Stamens, anthers.* — Medium size. Color—Plate 4, Light Cadmium. Arrangement—regular around styles.

*Stamens, filaments (threads).* — Medium length. Color—Plate 4, Lemon Yellow.

*Pollen.*—Plate 4, Lemon Chrome.

*Styles.*—Columnar, bunched; medium length; thin.

*Stigmas.*—Plate 5, Light Green Yellow.

*Ovaries.*—All enclosed in calyx.

Fruit:

Variety is fertile with its own pollen.

*Form.*—Round.

*Aspect.*—Smooth.

*Sepals.*—Permanent; straight.

*Plant*

Form:

Bush.

Growth:

Vigorous, upright, branching, compact.

Foliage:
5 to 7 leaflets.
*Size.*—Medium.
*Quantity.*—Normal.
*Color.*—New foliage: Upper side—between Plate 5, Calla Green and Plate 12, Blackish Red Purple. Under side—between Plate 27, Haematite Red and Plate 30, Brownish Olive. Old foliage: Upper side—Plate 41, Lincoln Green. Under side—Plate 31, Jade Green. *Shape.*—oval pointed. *Texture:* Upper side—glossy, flat. Under side—rough. Ribs and veins—prominent.
*Edge.*—Serrated (saw toothed).
*Serration.*—Single; small.
*Rachis.*—Color—Plate 31, Jade Green. Under side—prickles.
*Stipules.*—Short; smooth.
*Disease resistance.*—Slightly susceptible to black spot.
Wood:
*New Wood.*—Color—between Plate 27, Haematite Red and Plate 30, Brownish Olive. Bark—smooth.
*Old Wood.*—Color—Plate 41, Lincoln Green. Bark—smooth.
Thorns (divided into thorns, prickles and short needles):
*Thorns.*—Quantity: On main stalks from base—ordinary. On laterals from stalk—ordinary. Form—broad base; medium length, hooked downward. Color when young—Plate 27, Deep Corinthian Red. Position—irregular.
*Prickles.*—Quantity: On main stalks—none. On laterals—none. Color—Plate 4, Citrine.
*Short Needles.*—Quantity: On main stalks—few. On laterals—none.

What is claimed is:

A new and distinct variety of rose plant, of the Polyantha group, characterized as to novelty by its compact and bushy growth, and its continuous production of large pink colored flowers in large clusters, substantially as shown and described.

FANNIE NICOLAS,
*Administratrix of the Estate of Jean H. Nicolas, Deceased.*